United States Patent [19]

Schieferstein et al.

[11] Patent Number: 4,650,602

[45] Date of Patent: Mar. 17, 1987

[54] BLOCK-COPOLYMERIC POLYGLYCOL ETHERS AS SOLUTION PROMOTERS FOR OIL-SOLUBLE PERFUME OILS

[75] Inventors: Ludwig Schieferstein, Wuppertal; Ulrich Zeidler, Duesseldorf; Hermann Hensen, Hilden, all of Fed. Rep. of Germany

[73] Assignee: Henkel Kommanditgesellschaft auf Aktien, Duesseldorf, Fed. Rep. of Germany

[21] Appl. No.: 733,563

[22] Filed: May 13, 1985

[30] Foreign Application Priority Data

May 14, 1984 [DE] Fed. Rep. of Germany ....... 3417819

[51] Int. Cl.$^4$ ............................................. A61K 7/46
[52] U.S. Cl. ............................................. 252/522 R
[58] Field of Search .......................... 252/522 A, 522 R

[56] References Cited

U.S. PATENT DOCUMENTS

| | | | |
|---|---|---|---|
| 3,943,178 | 3/1976 | Stein et al. | 260/615 B |
| 3,956,401 | 5/1976 | Scardera et al. | 568/625 |
| 4,303,544 | 12/1981 | Kosswig et al. | 568/625 X |
| 4,479,887 | 10/1984 | Seibert | 252/309 |

OTHER PUBLICATIONS

McCutcheons Emulsifiers and Detergents, MC Publishing Co., Glenrock, N.J. USA (1984).

Primary Examiner—Bernard Helfin
Attorney, Agent, or Firm—Ernest G. Szoke; Henry E. Millson, Jr.; Mark A. Greenfield

[57] ABSTRACT

Block-copolymeric polyglycol ethers of long-chain 1,2-epoxides and ethylene oxide corresponding to the following general formula

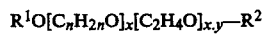

$$R^1O[C_nH_{2n}O]_x[C_2H_4O]_{x \cdot y}-R^2$$

in which one of the groups $R^1$ or $R^2$ is an alkyl or alkoxyalkyl group containing from 1 to 22 carbon atoms and the other is hydrogen, n is a number of from 6 to 22, x is a number of from 2 to 20 and y is a number of from 1 to 100, are useful as solution promoters for the preparation of clear, stable, aqueous or aqueous-alcoholic preparations containing oil-soluble perfume oils. Preferably, $R^1$ is an alkyl group, for example a methyl group, and $R^2$ is hydrogen.

8 Claims, No Drawings

BLOCK-COPOLYMERIC POLYGLYCOL ETHERS AS SOLUTION PROMOTERS FOR OIL-SOLUBLE PERFUME OILS

BACKGROUND OF THE INVENTION

1. Field of the Invention

This invention relates to the use of block-copolymeric polyglycol ethers of 1,2-epoxyalkanes and ethylene oxide as solution promoters for oil-soluble perfume oils.

2. Description of Related Art

For perfuming clear, aqueous cosmetic preparations, such as for example foam-bath and scented-bath preparations, shampoos, liquid soaps, skin cleansing preparations, or aqueous-alcoholic cosmetic preparations, such as face lotions, shaving lotions, toilet waters, hair lotions, etc., the perfume oils, which are generally oil-soluble ethereal oils, have to be clearly solubilized in the preparation. The type and quantity of surfactants and/or solvents present in the preparations is often not sufficient to solubilize the oilsoluble perfume oils in the requisite quantity. For this reason, solution-promoting compounds, i.e., so-called solution promoters or solubilizers, have to be used.

It is known that nonionic surfactants, for example sorbitan fatty acid esters and ethoxylates thereof and ethoxylates of hydrogenated castor oil, may be used as solubilizers for perfume oils. A major disadvantage of many solution promoters is that they have to be added in relatively large quantities to solubilize the desired quantity of perfume oil. Another disadvantage of many solution promoters is that their solubilizing effect is highly specific and applies only to individual perfume oils. In addition, the ethoxylates of hydrogenated castor oil have the disadvantage that, as derivatives of castor oil, a naturally occurring substance, they are subject to fluctuating availability and hence to the fluctuating price of that vegetable oil.

Accordingly, there is an urgent need for solution promoters for perfume oils which, when used in small quantities, have a good solubilizing effect on numerous oil-soluble perfume oils for the preparation of stable, clear, aqueous or aqueous-alcoholic preparations containing oil-soluble perfume oils.

DESCRIPTION OF THE INVENTION

Other than in the operating examples, or where otherwise indicated, all numbers expressing quantities of ingredients or reaction conditions used herein are to be understood as modified in all instances by the term "about".

It has now been found that block-copolymeric polyglycol ethers of long-chain 1,2-epoxyalkanes and ethylene oxide satisfy the requirements stated above to a high degree.

Accordingly, the present invention relates to the use of block-copolymeric polyglycol ethers of long-chain 1,2-epoxyalkanes and ethylene oxide corresponding to the following general formula $$R^1-O[C_nH_{2n}O]_x[C_2H_4O]_{x \cdot y}-R^2 \qquad (I)$$

in which one of the groups $R^1$ or $R^2$ is hydrogen and the other is a $C_1$-$C_{22}$ alkyl group or an alkoxyalkyl group such as a $C_1$-$C_6$-alkoxy-$C_2$-$C_6$-alkyl group or a $C_1$-$C_6$-alkoxy-$C_2$-$C_6$-alkoxy-$C_2$-$C_6$-alkyl group; n is a number of from 6 to 22; x is a number of from 2 to 20, and y is a number of from 1 to 100, as solution promoters for oil-soluble perfume oils.

Block-copolymeric polyglycol ethers corresponding to general formula I, in which $R^1$ is hydrogen and $R^2$ is an alkyl group, are known, for example, from U.S. Pat. No. 4,479,887 which corresponds to published German application No. 32 07 612. They are produced by addition of x moles of long-chain 1,2-epoxyalkanes corresponding to the general formula $C_nH_{2n}O$ onto alkyl polyglycol ethers corresponding to the following general formula

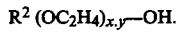

$$R^2(OC_2H_4)_{x \cdot y}-OH.$$

Block-copolymeric polyglycol ethers corresponding to general formula I, in which $R^1$ is an alkyl group or an alkoxyalkyl group and $R^2$ is hydrogen, are particularly suitable as solution promoters for oil-soluble perfume oils. They can be prepared by heating x moles of a linear 1,2-epoxyalkane containing n carbon atoms at a temperature of from 100° to 200° C. in the presence of from 0.1 to 20 mole % of a starting alcohol $R^1$—OH and from 0.1 to 5 mole % of a basic catalyst until no more epoxide oxygen can be detected and allowing x.y moles of ethylene oxide to act on the polymer formed in a pressure vessel at a temperature of from 100° to 200° C.; $R^1$, n, x and y having the meanings defined above.

α-olefin epoxides of the type obtainable by epoxidation in known manner of $C_6$-$C_{22}$ α-olefins can be used as the linear 1,2-epoxyalkanes. Mixtures of 1,2-epoxyalkanes having various alkyl chain lengths within the above range, of the type obtainable by expoxidation of commercial α-olefin cuts, can also be used herein.

In principle, the nature of the starting alcohol is not critical. Polymerization may be started with any monohydric alcohols which are suitable for opening the epoxide ring under the reaction conditions. Suitable alcohols of this type are, for example, methanol, ethanol, 2-ethylhexanol, n-dodecanol, stearyl alcohol, behenyl alcohol. However, methyl glycol, butyl glycol and butyl diglycol are also suitable alcohols. It is preferred to use $C_1$-$C_{22}$ alcohols, particularly methanol.

The basic catalysts used can be alkali metal hydroxides, alkali metal alcoholates, alkali metal and alkaline-earth metal salts of organic acids, for example sodium acetate or calcium acetate. Alkali metal alcoholates, preferably alcoholates of the starting alcohol, are particularly suitable. Sodium methylate is the most suitable basic catalyst.

To polymerize the 1,2-epoxyalkane, the reaction mixture is heated to a temperature above 100° C., optionally in a pressure vessel. The reaction is over when the 1,2-epoxyalkane has been reacted, i.e. when no more free epoxide oxygen can be detected in the reaction mixture. This takes about 1 to 10 hours at temperatures of from 100° to 200° C. and about 3 hours at a temperature of, for example, 150° C.

It is of course also possible to terminate polymerization of the 1,2-epoxyalkane before the 1,2-epoxyalkane has been completely reacted and to separate unreacted 1,2-epoxyalkane from the reaction mixture by distillation under reduced pressure. In that case, the average degrees of polymerization obtained are of course lower.

Ethylene oxide is then introduced under pressure onto the polymer formed, which still contains the basic catalyst, in a pressure vessel at temperatures of from 100° C. to 200° C. and preferably at temperatures of from 140° C. to 180° C. Where the starting material is a 1,2-epoxyalkane polymer which has been freed from the catalyst, another 2 to 5 mole % of a known basic or acidic ethoxylation catalyst has to be added before ethoxylation. The end of the addition of the ethylene oxide can be determined from the resulting drop in pressure.

It is clear that the values for x and y in formula I are average values because the polymerization or, more specifically, the addition of alkylene oxides always leads to mixtures of homologs in which the homologs are statistically distributed.

In the block-copolymeric polyglycol ethers corresponding to formula I, in which $R^2$ is hydrogen, the average degree of polymerization of the 1,2-epoxyalkane can be influenced by the quantity of starting alcohol. Small additions of from about 0.1 to 10 mole % of starting alcohol lead to average degrees of polymerization x of greater than 10, while relatively large additions of starting alcohol of from 10 to 20 mole % lead to average degrees of polymerization x of less than 10.

Mixtures of polyglycol ethers which correspond to general formula I, where $R^2$ is hydrogen with the block-copolymeric polyglycol ethers and compounds of the type known from U.S. Pat. No. 3,943,178 and equivalent German Pat. No. 2,331,014 in which the average degree of polymerization x is between 1 and 2 also fall within the scope of the invention.

The block-copolymeric polyglycol ethers of Formula I obtainable by the above described processes are soft to wax-like solid compositions whose solubility in water increases with the quantity of ethylene oxide added. The products show surface-active properties. With low contents of added ethylene oxide, they can be used as water-in-oil (W/O) emulsifiers; with higher contents of ethylene oxide, for example 10 moles and more per mole of 1,2-epoxyalkane, they can be used as oil-in-water (O/W) emulsifiers. It has been found that O/W emulsions prepared with the block copolymers as emulsifiers show particularly high thermal stability.

However, the solubilizing effect of the block-copolymeric polyglycol ethers on perfume oils is particularly pronounced.

Even when used in relatively small quantities, the block-copolymeric polyglycol ethers enable clear, stable, aqueous and aqueous-alcoholic preparations containing oil-soluble ethereal oils and perfume oils to be prepared. Aqueous-alcoholic preparations are understood to be preparations in mixtures of water and lower alcohols, such as ethanol and isopropanol. In this connection, the water and the lower alcohol can be mixed in any ratio, although they are preferably mixed in a ratio of from 90:10 to 10:90. To produce clear, stable, aqueous and aqueous-alcoholic preparations, quantities of from 0.1 to 10% by weight of the perfume oils must be clearly solubilized, although quantities of from 0.5 to 2.0% by weight of clearly solubilized perfume oil are sufficient for most purposes.

Quantities of only 0.3 to 5.0 parts by weight of the polyglycol ethers corresponding to general formula I, based on 1 part by weight of perfume oil, are sufficient for clearly solubilizing many ethereal oils. Polyglycol ethers corresponding to general formula I, in which n is a number of from 8 to 16, x is a number of from 2 to 10 and y is a number of from 10 to 50, have a particularly pronounced solubilizing effect on perfume oils.

The following Examples are intended to illustrate the invention without limiting it in any way.

EXAMPLES

1. Production of block-copolymeric polyglycol ethers (in which $R^2$ in Formula I is hydrogen)

Procedure for product 1.4 (Table I)

In a steel autoclave, 184 g (1.0 mole) of 1-epoxydodecane and 5.6 g of a 30% by weight methanolic solution of sodium methylate (0.03 mole of Na methylate) was heated with stirring for 3 hours to 150° C. Thereafter, no more epoxide oxygen could be detected in a sample of the reaction mixture. 880 g (20 moles) of ethylene oxide were then gradually introduced in portions under pressure at 150° C. After 5 hours, the drop in pressure showed that the ethylene oxide had been reacted.

After cooling and venting, a wax-like, water soluble product having a hydroxyl number of 12 was obtained.

The average degree of polymerization x of the α-epoxide may be estimated as follows from the molecular weight of the α-epoxide (EPO), the ethylene oxide (EO), the polyglycol ether (MG) according to the hydroxyl number and the molar quantity y of ethylene oxide added per mole of α-epoxide:

$$X = \frac{MG}{EPO + y\,EO}$$

(The proportion by weight of starting alcohol ($CH_3OH$) is disregarded.)

1.1–1.9 (Table I)

The block-copolymeric polyglycol ethers listed in the following Table I were produced by the method described above. In every case, methanol was used as the starting alcohol.

In the examples the following quantities of methanol (20% of which were in the form of sodium methylate) in moles per mole of 1,2-epoxyalkane were applied

| Example |
|---|
| 1.1:0.17 |
| 1.2:0.15 |
| 1.3:0.16 |
| 1.4:0.15 |
| 1.5:0.20 |
| 1.6:0.12 |
| 1.7:0.12 |
| 1.8:0.12 |
| 1.9:0.18 |

TABLE I

| No. | 1,2-epoxy linear alkane (n) | EO added (moles per mole of epoxide) (y) | OH No. | x | Quality | 10% by weight in water |
|---|---|---|---|---|---|---|
| 1.1 | 8 | 10 | 30 | 3.28 | wax-like, solid | clearly dissolved |
| 1.2 | 12 | 5 | 34.5 | 4.02 | soft mass | clouded solution |
| 1.3 | 12 | 10 | 24.9 | 3.60 | wax-like, solid | clouded solution |
| 1.4 | 12 | 20 | 12.0 | 4.38 | wax-like, solid | clearly dissolved |

TABLE I-continued

| No. | 1,2-epoxy linear alkane (n) | EO added (moles per mole of epoxide) (y) | OH No. | x | Quality | 10% by weight in water |
|---|---|---|---|---|---|---|
| 1.5 | 12 | 50 | 14.0 | 1.68 | wax-like, solid | clearly dissolved |
| 1.6 | 16 | 1 | 29.5 | 6.68 | soft mass | clouded with sediment |
| 1.7 | 16 | 5 | 19.9 | 6.12 | soft mass | clouded with sediment |
| 1.8 | 16 | 10 | 11.9 | 6.92 | wax-like, solid | clouded with sediment |
| 1.9 | 16 | 50 | 9.4 | 2.44 | wax-like, solid | clearly dissolved |

2. Solubilizing effect on perfume oils

The solubilizing effect of the block-copolymeric polyglycol ethers on perfume oils was tested as follows:

Mixtures of 1 g of certain, fat-soluble perfume oils and increasing quantities (for example 1 g, 2 g, 3 g, 4 g, etc.) of the solution promoter (polyglycol ether) were prepared. Each of these mixtures was then made up to 100 g with water or with a water-alcohol solvent mixture. Solutions of 1% by weight of the perfume oil were obtained in this way. Beyond a certain solution promoter content sufficient for solubilization, the solutions obtained were clear at 20° C. This quantity of solubilizer required for clearly solubilizing 1% by weight of the particular perfume oil is shown in Table II for some of the polyglycol ethers of the invention listed in Table I on the basis of the solvent mixtures set forth therein. The values obtained for a commercial perfume oil solubilizer—the adduct of 60 moles of ethylene oxide with hydrogenated castor oil ("RH 60")—are shown for comparison.

The following perfume oils were used:

| | |
|---|---|
| A pine oil | F bergamot oil |
| B clove leaf oil | G cedar wood oil |
| C rosemary oil | H patchouli oil |
| D lavandin oil | J lemon oil |
| E peppermint oil | K orange oil |

TABLE II

| Solution promoter | Solvent water:ethanol (% by weight) | Quantity (% by weight) of solution promoter required for solubilizing 1% by weight of perfume oil (A-K) | | | | | | | | |
|---|---|---|---|---|---|---|---|---|---|---|
| | | A | B | C | D | E | F | G | H | J | K |
| 1.1 | 75:25 | 1 | 2 | 2 | 2 | 2 | 2 | 4 | 4 | 1 | 3 |
| 1.3 | 75:25 | 1 | 2 | 2 | 2 | 2 | 4 | 7 | 7 | 3 | 5 |
| 1.4 | 75:25 | 1 | 2 | 2 | 2 | 2 | 3 | 5 | >7* | 2 | 2 |
| 1.5 | 75:25 | 3 | 3 | 2 | >7 | 5 | 3 | >7 | >7 | 4 | 3 |
| 1.9 | 75:25 | 3 | 3 | 1 | 7 | 4 | 3 | >7 | 7 | 2 | 3 |
| "RH 60" | 75:25 | 1 | 3 | 2 | 2 | 1 | 2 | 5 | 2 | 2 | 2 |
| 1.4 | 35:65 | 1 | 1 | 1 | 1 | 1 | 1 | 1 | 1 | 1 | 1 |
| 1.5 | 35:65 | 1 | 1 | 1 | 1 | 1 | 2 | 2 | 4 | 2 | 2 |
| 1.9 | 35:65 | 1 | 1 | 1 | 1 | 1 | 2 | 2 | 2 | 2 | 2 |
| "RH 60" | 35:65 | 1 | 1 | 1 | 1 | 1 | 1 | 2 | 2 | 1 | 1 |

*>7 means that the solution obtained with 7% by weight of solution promoter was not completely clear (at 20° C.)

What is claimed is:

1. A clear aqueous or aqueous-alcohol composition comprising:
   a. at least one oil-soluble perfume oil, and
   b. from about 0.3 to about 5 parts by weight, based on 1 part by weight of a., of at least one block-copolymeric polyglycol ether of the formula:

$$R^1-O-[C_nH_{2n}O]_x[C_2H_4O]_{x,y}R^2 \quad (I)$$

wherein $R^1$ or $R^2$ is hydrogen, and the other R group is a $C_1$-$C_{22}$ alkyl group or an alkoxyalkyl group, n is an integer of from 6 to 22, x is a number of from 2 to 20, and y is a number of from 1 to 100.

2. A composition in accordance with claim 1 wherein in b. $R^2$ is hydrogen.

3. A composition in accordance with claim 2 wherein $R^1$ is methyl.

4. A composition in accordance with claim 1 wherein in b. n is an integer of from 8 to 16, x is a number of from 2 to 10, and y is a number of from 10 to 50.

5. A method for solubilizing oil-soluble perfume oils in water or water-alcohol compositions comprising forming a water or water-alcohol composition containing:
   a. at least one oil-soluble perfume oil, and
   b. from about 0.3 to about 5 parts by weight, based on 1 part by weight of a., of at least one block-copolymeric polyglycol ether of the formula:

$$R^1-O-[C_nH_{2n}O]_x[C_2H_4O]_{x,y}R^2 \quad (I)$$

wherein $R^1$ or $R^2$ is hydrogen, and the other R group is a $C_1$-$C_{22}$ alkyl group or an alkoxyalkyl group, n is an integer of from 6 to 22, x is a number of from 2 to 20, and y is a number of from 1 to 100.

6. A method in accordance with claim 5 wherein in b. $R^2$ is hydrogen.

7. A method in accordance with claim 6 wherein $R^1$ is methyl.

8. A method in accordance with claim 5 wherein in b. n is an integer of from 8 to 16, x is a number of from 2 to 10, and y is a number of from 10 to 50.

* * * * *